United States Patent [19]

Kupperman et al.

[11] Patent Number: 4,898,034

[45] Date of Patent: Feb. 6, 1990

[54] HIGH TEMPERATURE ULTRASONIC TESTING OF MATERIALS FOR INTERNAL FLAWS

[75] Inventors: David S. Kupperman, Oak Park, Ill.; Melvin Linzer, Silver Spring, Md.

[73] Assignee: The United States of America as represented by the Department of Energy, Washington, D.C.

[21] Appl. No.: 235,078

[22] Filed: Aug. 23, 1988

[51] Int. Cl.⁴ .................. G01N 29/00; G01N 29/04
[52] U.S. Cl. .......................................... 73/644; 73/639
[58] Field of Search ............... 73/639, 644; 310/334, 310/335, 336

[56] References Cited

U.S. PATENT DOCUMENTS

| | | | |
|---|---|---|---|
| 3,621,709 | 11/1971 | Frey | 73/644 |
| 3,732,444 | 5/1973 | Miller | 73/644 |
| 4,160,387 | 7/1979 | Ihara et al. | 73/639 |
| 4,291,577 | 9/1981 | Baum et al. | 73/639 |
| 4,587,849 | 5/1986 | Gross | 73/644 |
| 4,703,656 | 11/1987 | Bhardwaj | 73/644 |

*Primary Examiner*—John Chapman
*Assistant Examiner*—Robert P. Bell
*Attorney, Agent, or Firm*—Robert J. Fisher; Hugh W. Glenn; William R. Moser

[57] ABSTRACT

An apparatus is disclosed for nondestructive evaluation of defects in hot materials, such as metals and ceramics, by sonic signals, which includes a zirconia buffer in contact with a hot material being tested, a liquid couplant of borax in contact with the zirconia buffer and the hot material to be tested, a transmitter mounted on the zirconia buffer sending sonic signals through the buffer and couplant into the hot material, and a receiver mounted on the zirconia buffer receiving sonic signals reflected from within the hot material through the couplant and the buffer.

18 Claims, 1 Drawing Sheet

HIGH TEMPERATURE ULTRASONIC TESTING OF MATERIALS FOR INTERNAL FLAWS

CONTRACTUAL ORIGIN OF THE INVENTION

The United States Government has rights in this invention pursuant to Contract No. W-31-109-ENG-38 between the U.S. Department of Energy and Argonne National Laboratory.

BACKGROUND OF THE INVENTION

The present invention relates to ultrasonic testing of high temperature materials, such as metals, ceramics and composite fabrications, in order to detect internal flaws. In particular, the present invention relates to the combination of a buffer and a couplant in an ultrasonic testing device which can detect flaws in steel at temperatures in the range from about 1700° F. to about 2200° F.

In the reheating method of converting steel from ingot to bloom or slab form after stripping, the ingots are held in the soaking pits of the blooming or slabbing mill, wherein they are brought to a uniform temperature of about 2400° F. The ingots are then removed from the soaking pit and placed on the entry roll table of the rolling mill. The ingots are passed along the roller table to the reducing stand which shapes the ingots into the blooms or slabs. The bloom or slab workpiece is advanced toward a cutting device, such as a crop shear or a cutting torch, at the end of the mill roller table. The cutting device severs the product to the designated length by cropping sufficient scrap from the two ends of the product to correspond to what was the top and the bottom of the original ingot. This cropping of the workpiece insures the elimination of primary pipe, mechanical foldover or fish tail, porosity, and other similar defects.

In the continuous casting of steel, changes can occur in the internal quality of the cast steel because of changes made in the continuous casting process to compensate for variations which may occur in the thermal and metallurgical characteristics of the process. Anomalies such as subsurface cracks, internal cleanliness and/or center looseness or porosity must be detected prior to shipment of the product. It is well recognized that with a suitable sensor for hot in-line detection of such internal discontinuities, process control action could be initiated immediately to correct these deficiencies in quality. In addition, a computer based system could immediately readjust cut length at the runout in order to compensate for steel which has been removed by the cropping shear or cutting torch because of poor internal quality.

The problem of accurately determining the optimum cropping point in the hot steel products has plagued the steel industry for years. The location of this optimum cropping point is in the sound product just beyond the extent of the flaw. Traditionally, locating the cropping point has been dependent upon the experience and judgment of the cropping shear operator. He would often have to shear the product more than once before he would cut through sound product. This procedure resulted in a waste of the operator's time as well as in a reduction of product yield.

It has been estimated that the capability of effectively exercising process control to rapidly compensate for internal quality changes sensed in-line would represent, conservatively, an improvement of 1% in yield. In a typical steel producing installation, such an improvement could represent an annual savings of 1.0 to 1.4 million dollars per year.

Ultrasonic transducers are commercially available which can scan a relatively cold slab, bloom or billet and reveal any internal nonhomogeneous portions of the product, since an acoustic couple can be easily achieved with the cold steel. The use of ultrasonics in testing steel products at relatively high temperatures is a different matter, however. Many investigators have tried ultrasonics but have encountered problems in attempting to achieve a proper acoustic couple between the workpiece and the ultrasonic transducer. Normal production temperatures of about 1950° F. are detrimental to transducers commercially available and, therefore, proper intimate contact between the product and the transducer to form the acoustic couple is very difficult. Without the necessary acoustic couple, an accurate determination of any flaw in the workpiece is not possible.

In one device for severing hot steel, an ultrasonic transducer is fitted with a water jacket and then embedded in one of the blades of a crop shear. When the shear blade contacts the hot workpiece with sufficient pressure, an acoustic couple is formed between the transducer and the workpiece through the shear blade. Before the cut is made, the sheer operator is able to ultrasonically scan the hot workpiece to determine the optimum cropping length for the elimination of flaws from the workpiece. This system is disclosed in U.S. Pat. No. 4,175 442 to Terry.

A more recent device which is capable of detecting flaws within the hot steel workpiece by ultrasonic testing was demonstrated at Argonne National Laboratory in June of 1986. This device is the result of funding by the American Iron And Steel Institute and a cooperative technical effort between Magnaflux Corporation (Chicago, Illinois), Argonne National Laboratory (Argonne, Illinois) and the National Bureau of Standards (Gaithersburg, Maryland). The device is called a Rolling Contact Ultrasonic Transducer, and it can detect flaws as small as ¼ inch in steel at temperatures of about 2000° F. The ultrasonic transducer which generates the sound waves is placed in contact with the inside rim of a thermal buffer comprising a large stainless steel wheel having a diameter of three feet. With a cooling system, the transducer is maintained cool enough to carry out an inspection of the hot steel. The buffer wheel is rolled by means of computer control over the hot slab or billet to be tested. Sound waves travel through the wheel rim and into the hot steel directly by high pressure contact between the wheel and the billet. The contact between the wheel and the billet is enhanced to an elevated pressure by a hydraulic mechanism which presses the wheel tightly down upon the surface of the hot steel billet. Sound waves reflecting off of defects within the hot steel can be observed on the monitor of a small computer. A color defect map of the steel can be generated by the computer and this color map clearly defines the bad region of the specimen which must then be severed from the billet. This device was disclosed in a paper delivered at the University of California, San Diego, on Aug. 3–8, 1986, during a conference entitled "Review Of Progress in Nondestructive Evaluation". The paper was entitled "Advances In The Development Of An In-Line Sensor System For The Internal Inspection Of Hot Steel".

With this then being the state of the art, it is an object of the present invention to provide an improved apparatus for detecting internal flaws within hot materials, such as metals, ceramics, and composite fabrications such as laminates or metal matrices.

It is another object of the present invention to provide an improved apparatus for detecting internal flaws within hot materials wherein no cooling system is required for the detection apparatus.

It is a further object of the present invention to provide an improved apparatus for detecting internal flaws within hot materials wherein no hydraulic system is required to push the detector tightly against the workpiece in order to obtain a good couple for transmitting sound into the workpiece being tested.

These and other objects of the present invention, as well as the advantages thereof, will become more clear from the description which follows.

SUMMARY OF THE INVENTION

The present invention provides a significant improvement in the ability to inspect hot materials such as hot steel slabs with ultrasonic waves. In particular the invention utilizes the concept of a buffer and a couplant.

In contrast to the above described prior art device wherein a stainless steel buffer wheel was used, the present invention utilizes a buffer comprising zirconia (zirconium oxide). A zirconia buffer better isolates the ultrasonic transducer from the heat of the slab while at the same time providing good acoustic properties. The zirconia buffer provides good transmission of ultrasonic waves with low attenuation and low thermal conductivity.

In addition, borax (sodium tetraborate) is employed as a liquid couplant in order to eliminate the need for a high pressure hydraulic system to couple the buffer to the hot slab. Borax is inexpensive and a powder at room temperature, but it is a liquid in the temperature range of from about 1700° to about 2200° F., which is the temperature range of hot steel slabs during ultrasonic inspection. Additionally, borax has good chemical stability and desirable viscosity characteristics at the conditions experienced during the ultrasonic inspection of the hot steel.

With this unique combination of buffer material and couplant material, many improvements are accomplished. The transducer is isolated more effectively from the heat of the steel slab. This is the result of the lower thermal conductivity of the zirconia compared to stainless steel. The powerful cooling system which is required when stainless steel is used for the buffer wheel can be eliminated when zirconia is used. In addition, zirconia has better properties with respect to the propagation of ultrasonic waves and, as a result, larger ultrasonic signals are available for analysis. Moreover, zirconia has good chemical stability and it is noncorrosive with other materials in the test environment.

With borax as the liquid couplant at the temperature of the steel slab, there is no need for a hydraulic system to exert force on the buffer in order to couple the sound into the steel slab by a high pressure contact. This reduces the cost and simplifies the system. Tests conducted at Argonne National Laboratory using borax and zirconia also showed that this combination of buffer and couplant was more effective than stainless steel and borax because of the reduction in corrosion products.

The combination of zirconia buffer with the liquid borax coupler also enhances detection sensitivity, since internal defects within the hot steel workpiece may be as small as 3 mm and still be detected.

Accordingly, in one embodiment the present invention comprehends an apparatus for conducting sonic signals into and from hot materials, such as metals and ceramics, which comprises a zirconia buffer in contact with a hot material and conducting sonic signals into and from the hot material.

In another embodiment the present invention comprehends an apparatus for conducting sonic signals into hot materials, such as metals and ceramics, which comprises a buffer in contact with a hot material, and a liquid couplant comprising borax in contact with the buffer and the hot material, whereby sonic signals are passed into and returned from the hot material by means of the buffer and the liquid borax couplant.

In a further embodiment, the present invention comprehends an apparatus for nondestructive evaluation of defects in hot materials, such as metals and ceramics, by sonic signals, which comprises in combination, a zirconia buffer in contact with a hot material to be tested for defects; a liquid couplant comprising borax, in contact with the zirconia buffer and the hot material to be tested; transmitting means mounted on the zirconia buffer and spaced from the hot material to be tested, the transmitting means sending sonic signals through the buffer and the couplant, and into the hot material to be tested; and receiving means mounted on the zirconia buffer and spaced from the hot material to be tested, the receiving means receiving sonic signals reflected from within the hot material to be tested, through the couplant and the buffer.

In another embodiment of the present invention, the zirconia buffer is passed across the hot material while in direct contact with the hot material. The zirconia buffer may be a wheel rolling on a surface of the hot material or it may comprise a shoe sliding across the surface of the hot material.

In a further embodiment of the present invention, the zirconia buffer is maintained in a fixed position and the hot material is moved across the buffer while in direct contact with the buffer. The zirconia buffer may comprise a wheel rolling on the surface of the moving hot material or it may comprise a shoe in sliding contact with a surface of the moving hot material.

Alternatively, the zirconia buffer and the hot material to be tested may be fixed in a stationary position while the apparatus sends the sonic signals and receives reflected signals which portray the flaws within the material being tested.

A clearer understanding of the present invention will be obtained from the disclosure which follows when read in light of the accompanying drawings.

DESCRIPTION OF THE PREFERRED EMBODIMENTS

Figure 1:
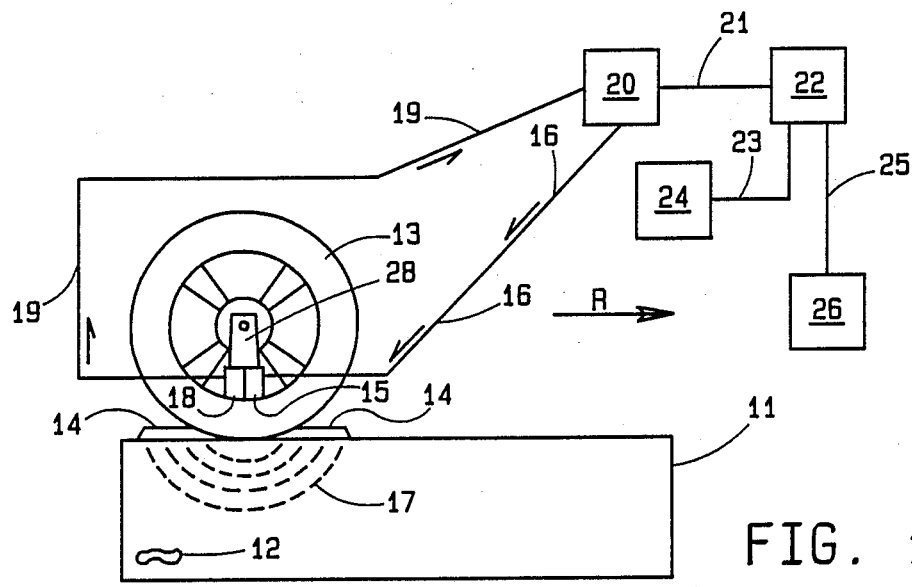
FIG. 1 is a simplified schematic representation of a first embodiment of the inventive apparatus.

Referring now to FIG. 1, there is shown a slab or billet 11 in a fixed position. The slab 11 contains a void or other flaw 12 deep within its structure. A zirconia buffer comprising a sensor wheel 13 rolls clockwise across the slab 11 in the direction R, as indicated by the arrow. The buffer wheel is in contact with a molten borax couplant 14 which enhances the transmission of ultrasonic signals into the steel slab 11.

The ultrasonic signals are transmitted by a transducer 15 mounted on the inside rim of the zirconia wheel 13. The transducer 15 provides pulsing ultrasonic signals responsive to electrical pulses which enter the transducer by means of a transmitting cable 16. The ultrasonic wave pulses are shown in the slab 11 as a series of broken elliptical lines 17. A receiving transducer 18 is also located on the inside rim of the buffer wheel 13. The receiving transducer receives the reflected ultrasonic wave pulses emerging from within the slab 11. The transducer 18 converts the ultrasonic pulses into a pulsing electrical signal which is transmitted by means of a cable 19 to an interfacing unit 20.

The interfacing unit 20 continuously transmits pulse signals electrically via cable 16 to transducer 15, and it receives the electrical pulse signals representative of the reflected ultrasonic wave pulses via the cable 19. The interfacing unit also includes peak detection means. Interfacing unit 20 is coupled to a computer 22 by means of cable 21. Computer 22 is programed to control the rolling of buffer wheel 13 by conventional motive means not shown, and to control the output electrical pulses transmitted to the transducer 15 via cable 16. The computer 22 receives signals from the interfacing unit 20 which are representative of the ultrasonic signals reflected from within the steel slab 11. The computer 22 processes this information and transmits output signals via cable 23 to a visual display unit 24 (a cathode-ray tube display device) for exhibiting a defect map of the slab or billet 11. Each imperfection or flaw is outlined and its shape, size and location is shown on the viewing screen. Although the defect map may be displayed as a monochrome image (black and white) on the viewing screen, it is preferred that the visual display unit 24 exhibit a colorgraphic defect map. Alternatively, the viewing screen may provide a numeric display. Additionally, as may be desired, the computer 22 transmits signals via cable 25 to a printer 26. Printer 26 provides a hard copy printout of data representative of the flaw detection for the slab or billet 11.

A stationary bracket 28 is mounted at the axle of the buffer wheel 13. The bracket 28 holds the transducers 15 and 18 tightly against the inner rim of the zirconia buffer wheel 13 in a fixed position so that, as the wheel rolls clockwise, the transducers will remain constantly fixed at the 6 o'clock position. Thus, the transducers are retained at the bottom of the wheel in sliding contact at all times. This minimizes the distance along which the ultrasonic signals must pass from the transducer 15 into the slab 11, and from the slab back to transducer 18.

Figure 2:
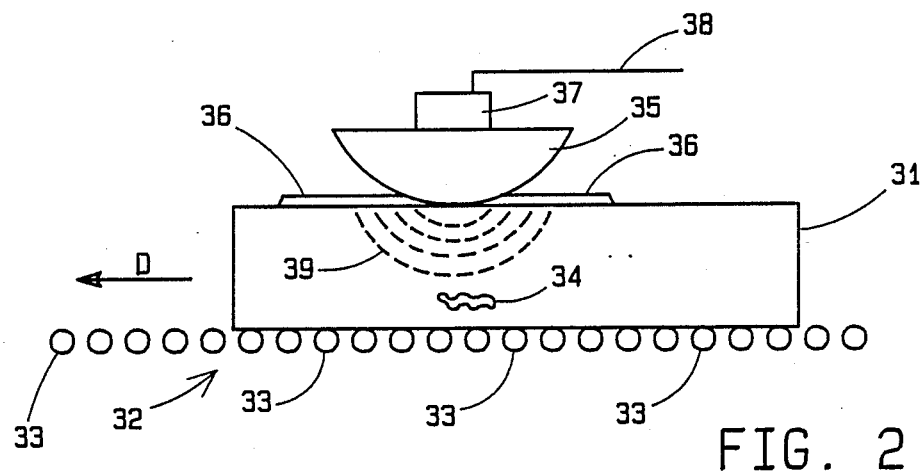
FIG. 2 is a simplified schematic representation of a second embodiment of the inventive apparatus.

FIG. 2 illustrates an alternate embodiment of the invention. In this embodiment a slab or billet 31 of hot steel is moved on a conventional roller conveyor 32 comprising a plurality of rolls 33 in a direction D, as indicated by the arrow. The slab or billet 31 contains a void or other flaw 34. The zirconia buffer 35 is in a fixed position and rides on the moving billet 31 as a shoe. This shoe is shown in FIG. 2 as having the shape of a segment of a cylinder. Alternatively, the shoe could have the shape of a wedge or of a rod. The shape of the shoe is not critical so long as the zirconia buffer is capable of sliding on the surface of the slab 31 with a small contact area. A borax liquid couplant 36 is located on the surface of the slab 31 in contact with the shoe 35. A transducer 37 is mounted on the top of the zirconia buffer 35. The transducer is a piezoelectric transducer which is capable of receiving a pulsing electric signal via means 38 and converting this signal into a pulsing ultrasonic signal. The pulsing ultrasonic signal passes through the zirconia buffer 35 and the liquid borax couplant 36, and then enters the hot steel slab 31. The pulsing ultrasonic signal is represented by a series of broken elliptical lines 39. Ultrasonic signals 39 are reflected from the flaw 34 within the slab 31 and back through the borax couplant 36 and the zirconia buffer 35. The pulsing ultrasonic signals are picked up by the piezoelectric transducer 37 and are converted to pulsing electrical signals which are then passed via cable 38 to the interfacing means 20 (not shown in FIG. 2). In this embodiment, only the single transducer 37 and the single cable 38 are used. The transducer receives and sends electrical pulses alternatively.

Figure 3:
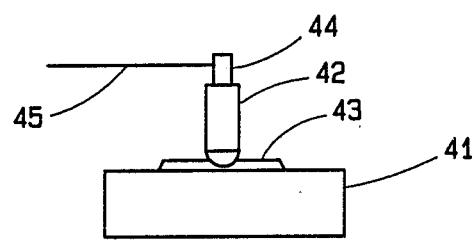
FIG. 3 is a simplified schematic representation of a still further embodiment of the inventive apparatus.

FIG. 3 illustrates an alternate embodiment of the invention wherein the ultrasonic testing of the hot steel is conducted with both the steel slab 41 and the zirconia coupler 42 held in a fixed position. The zirconia buffer 42 has the shape of a rod or cylinder which has a rounded or hemispherical tip. Liquid borax couplant 43 surrounds the point of contact between the buffer 42 and the hot steel slab 41. The zirconia buffer 42 has a piezoelectric transducer 44 mounted thereon. The transducer receives electrical signals via cable 45 and converts them to ultrasonic pulses. The transducer 44 receives reflected ultrasonic pulses and converts them to electrical signals which are transmitted via cable 45 back to the interfacing unit 20 which is not shown in FIG. 3.

In the preferred embodiments of the present invention, the zirconia buffer should have a thickness at least as great as the thickness of the item being tested. That is to say, the distance between the transducer and the surface of the hot material tested should be about as great as the thickness of the hot material which is being tested. Although the foregoing description of the present invention shows a single zirconia buffer in each embodiment, it is within the scope of the present invention to have more than one zirconia buffer in the inventive device, such as a plurality of shoes riding on one or more surfaces of the hot workpiece.

The borax couplant which is utilized in the present invention forms a pool of liquid adjacent the point of contact between the zirconia buffer and the surface of the hot material being tested. This pool does not cover the entire surface of the hot material being tested but is only localized in the vicinity of the contact area. In those embodiments of the invention where motion occurs between the zirconia buffer and the surface of the hot material, there will be a tendency for the borax couplant to be wiped away from the surface at the contact point. Accordingly, it is necessary to periodically inject a fresh amount of borax liquid onto the surface of the hot workpiece when the relative motion between the zirconia buffer and the workpiece has wiped away too much of the borax liquid couplant. This is necessary in order to ensure that sufficient borax liquid couplant is positioned around the contact point at all times in order to provide for enhanced transmission of the ultrasonic sound waves between the zirconia buffer and the hot workpiece being tested. Means for applying additional liquid borax to the surface of the hot steel slab are not shown in the Figures, since such means are conventional.

It will be realized from the description hereinabove, that the transducers may be utilized as a pair consisting of a sending transducer and a receiving transducer, or as a single transducer which operates to both send and receive pulse signals in an alternating sequence. Thus, in the embodiment of FIG. 1 a transmitting transducer 15 and a receiving transducer 18 are shown, but a single transducer such as the piezoelectric transducer 37 of FIG. 2 could be utilized instead. Similarly, in FIG. 2 a single transmitting transducer 15 and a receiving transducer 18 could be utilized instead of the single piezoelectric transducer 37 which both receives and transmits signals. In any event, the use of the zirconia buffer and the borax couplant provides an improved means for coupling sonic signals in and out of the hot work piece independent of the specific design of the electronic circuitry.

Although the present invention has been described hereinabove in reference to the sending of pulsing ultrasonic signals through the zirconia buffer and the borax couplant, the invention is not so limited. The invention is directed to improved means of coupling sonic signals in and out of the hot workpiece. Thus, the pulsing ultrasonic signal may be replaced by a nonpulsing signal. The signal could be a continuous ultrasonic wave, but it need not be ultrasonic. The signal could comprise sound waves at different frequencies, other than ultrasonic.

The foregoing description of the invention relates to the sonic nondestructive evaluation of defects in hot steel products in the temperature range of from about 1700° F. to about 2200° F., but more normally in the range of from about 1800° F. to about 2000° F. However, the present invention also has utility in flaw detection for other hot metals, ceramics, and composite fabrications such as laminates and metal matrices. Additionally, this invention has application to high temperature sonic characterization or flaw detection of components both during and after fabrication.

In light of the foregoing disclosure, further alternative embodiments of the inventive ultrasonic detection apparatus will undoubtedly suggest themselves to those skilled in the art. It is thus intended that the disclosure be taken as illustrative only, and that it not be construed in any limiting sense. Modifications and variations may be resorted to without departing from the spirit and the scope of this invention, and such modifications and variations are considered to be within the purview and the scope of the appended claims.

The embodiments of this invention in which an exclusive property or privilege is claimed are defined as follows:

1. Apparatus for nondestructive evaluation of defects in hot materials, such as metals and ceramics, by sonic signals, which comprises in combination:
   (a) a buffer in contact with a hot material to be tested for defects, said hot material having a temperature in the range of from about 1700° F. to about 2200° F.;
   (b) a liquid couplant consisting essentially of borax, in contact with said buffer and said hot material to be tested;
   (c) transmitting means mounted on said buffer and spaced from said hot material to be tested, said transmitting means sending sonic signals through said buffer and said couplant, and into said hot material to be tested; and
   (d) receiving means mounted on said buffer and spaced from said hot material to be tested, said receiving means receiving sonic signals reflected from within said hot material to be tested, through said couplant and said buffer.

2. Apparatus according to claim 1 wherein said hot material is at a temperature in the range of from about 1800° F. to about 2000° F.

3. Apparatus for nondestructive evaluation of defects in hot materials, such as metals and ceramics, by sonic signals, which comprises in combination:
   (a) a zirconia buffer in contact with a hot material to be tested for defects, said hot material having a temperature in the range of from about 1700° F. to about 2200° F.;
   (b) a liquid couplant comprising borax, in contact with said zirconia buffer and said hot material to be tested;
   (c) transmitting means mounted on said zirconia buffer and spaced from said hot material to be tested, said transmitting means sending sonic signals through said buffer and said couplant, and into said hot material to be tested; and
   (d) receiving means mounted on said zirconia buffer and spaced from said hot material to be tested, said receiving means receiving sonic signals reflected from within said hot material to be tested, through said couplant and said buffer.

4. Apparatus according to claim 3 wherein said zirconia buffer and said hot material are in stationary contact.

5. Apparatus according to claim 3 wherein said zirconia buffer is passed across said hot material while in direct contact with said hot material.

6. Apparatus according to claim 3 wherein said zirconia buffer is maintained in a fixed position and said hot material is moved across said buffer while in direct contact with said buffer.

7. Apparatus according to claim 3 wherein said zirconia buffer comprises a wheel in rolling contact with a surface of said hot material.

8. Apparatus according to claim 3 wherein said zirconia buffer comprises a shoe in sliding contact with a surface of said hot material.

9. Apparatus according to claim 3 wherein said hot material is at a temperature in the range of from about 1800° F. to about 2000° F.

10. Apparatus according to claim 3 wherein said hot material comprises a ceramic.

11. Apparatus according to claim 3 wherein said hot material comprises a composite material.

12. Apparatus according to claim 3 wherein said hot material comprises a metal.

13. Apparatus according to claim 12 wherein said metal comprises steel.

14. Apparatus according to claim 13 wherein said steel is at a temperature of from about 1800° F. to about 2000° F.

15. Apparatus according to claim 3 wherein said transmitting means comprises a first transducer and said receiving means comprises a second transducer.

16. Apparatus according to claim 3 wherein a single transducer comprises said transmitting means and said receiving means.

17. Apparatus according to claim 3 including interfacing means, computer means, and readout means, said interfacing means receiving signals from said computer means and responsively sending signals to said computer means, said computer means processing said signals received from said interfacing means to detect flaws within said hot material and sending signals to said readout means to visually report said flaws.

18. Apparatus according to claim 17 wherein said readout means is selected from the group consisting of a cathoderay tube display device and a printing device.

* * * * *